United States Patent
Feldman et al.

(10) Patent No.: US 7,711,413 B2
(45) Date of Patent: May 4, 2010

(54) CATHETER IMAGING PROBE AND METHOD

(75) Inventors: Marc D. Feldman, San Antonio, TX (US); Thomas E. Milner, Austin, TX (US); Shaochen Chen, Austin, TX (US); Jeehyun Kim, Irvine, CA (US); Li-Hsin Han, Austin, TX (US); Jung-Hwan Oh, Austin, TX (US); Ho Lee, Austin, TX (US)

(73) Assignee: Volcano Corporation, San Antonio, TX (US)

( * ) Notice: Subject to any disclaimer, the term of this patent is extended or adjusted under 35 U.S.C. 154(b) by 573 days.

(21) Appl. No.: 10/548,982

(22) PCT Filed: Apr. 23, 2004

(86) PCT No.: PCT/US2004/012773

§ 371 (c)(1), (2), (4) Date: May 2, 2006

(87) PCT Pub. No.: WO2004/096049

PCT Pub. Date: Nov. 11, 2004

(65) Prior Publication Data

US 2006/0241493 A1 Oct. 26, 2006

Related U.S. Application Data

(60) Provisional application No. 60/466,215, filed on Apr. 28, 2003.

(51) Int. Cl.
*A61B 8/00* (2006.01)
*A61B 1/06* (2006.01)

(52) U.S. Cl. .................. 600/478; 600/466; 600/473; 600/182

(58) Field of Classification Search ............ 600/466, 600/467, 472, 473, 182; 623/2.11
See application file for complete search history.

(56) References Cited

U.S. PATENT DOCUMENTS 1,467,672 A * 9/1923 Kaplan .................. 415/129

(Continued)

FOREIGN PATENT DOCUMENTS

EP 147192 A * 7/1985

(Continued)

OTHER PUBLICATIONS

Driggers, Ronald G. (ed.) (2003). Encyclopedia of Optical Engineering. New York: Marcel Dekker. vol. 2, p. 1594.*

(Continued)

*Primary Examiner*—Eric F Winakur
*Assistant Examiner*—Helene Bor
(74) *Attorney, Agent, or Firm*—David G. Rosenbaum; J. Peter Paredes; Rosenbaum & Silvert, P.C.

(57) ABSTRACT

A catheter imaging probe for a patient. The probe includes a conduit through which energy is transmitted. The probe includes a first portion through which the conduit extends. The probe includes a second portion which rotates relative to the conduit to redirect the energy from the conduit. A method for imaging a patient. The method includes the steps of inserting a catheter into the patient. There is the step of rotating a second portion of the catheter relative to a conduit extending through a first portion of the catheter, which redirects the energy transmitted through the conduit to the patient and receives the energy reflected back to the second portion from the patient and redirects the reflected energy to the conduit.

59 Claims, 9 Drawing Sheets

U.S. PATENT DOCUMENTS

| | | | | |
|---|---|---|---|---|
| 2,334,302 A | * | 11/1943 | Akins | 415/75 |
| 3,945,375 A | * | 3/1976 | Banko | 600/104 |
| 4,648,892 A | * | 3/1987 | Kittrell et al. | 65/387 |
| 5,176,141 A | * | 1/1993 | Bom et al. | 600/467 |
| 5,240,003 A | * | 8/1993 | Lancee et al. | 600/467 |
| 5,271,402 A | * | 12/1993 | Yeung et al. | 600/437 |
| 5,438,997 A | | 8/1995 | Sieben et al. | 128/662.06 |
| 5,507,294 A | * | 4/1996 | Lum et al. | 600/459 |
| 5,635,784 A | | 6/1997 | Seale | 310/90.5 |
| 6,001,112 A | * | 12/1999 | Taylor | 606/159 |
| 6,134,033 A | | 10/2000 | Bergano et al. | 359/122 |
| 6,264,608 B1 | * | 7/2001 | Schatzle et al. | 600/439 |
| 6,357,998 B1 | * | 3/2002 | Rosefsky | 415/66 |
| 2002/0198457 A1 | | 12/2002 | Tearney et al. | 600/476 |

FOREIGN PATENT DOCUMENTS

| | | |
|---|---|---|
| WO | 2004/096049 | 11/2004 |

OTHER PUBLICATIONS

Davies, Michael J., et al., "Plaque Fissuring—the cause of acute myocardial infarction, sudden ischaemic death, and crescendo agina", *Br Heart J*, vol. 53, pp. 363-373, (1985).

Davies, Michael J., et al., "Risk of thrombosis in human atherosclerotic plaques: role of extracellular lipid, macrophage, and smooth muscle cell content", *Br Heart J*, vol. 69, pp. 377-381, (1993).

Jang, I.K., et al., "Visualization of Cornoary Atheerosclerotic Plaques in Patients Using Optical Coherence Tomography: Comparison With Intravascular Ultrasound", *Journal of the American College of Cardiology*, vol. 29, No. 4, pp. 604-609 (2002).

Nisssen, Steven, "Coronary Angiography and Intravascular Ultrasound", *Am J Cardiol*, vol. 87 (suppl), pp. 15A-20A, (2001).

Rabbani, R., et al., "Strategies to achieve coronary arterial plaque stabilization", *Cardiovascular Research*, vol. 41, pp. 402-417 (1999).

Villard, Joseph W., et al., "Use of a Blood Substitute to Determine Instantaneous Murine Right Ventricular Thickening With Optical Coherence Tomography", *Circulation, Journal of the American Heart Association*, vol. 105, pp. 1843-1849 (2002).

Little, W.C., et al., "The underlying coronary lesion in myocardial infarction: implications for coronary angiography", *Cllin Cardiol*, vol. 14, No. 11, pp. 868-874, (Nov. 1991).

European Search Report, pp. 1-4 (Apr. 15, 2009).

\* cited by examiner

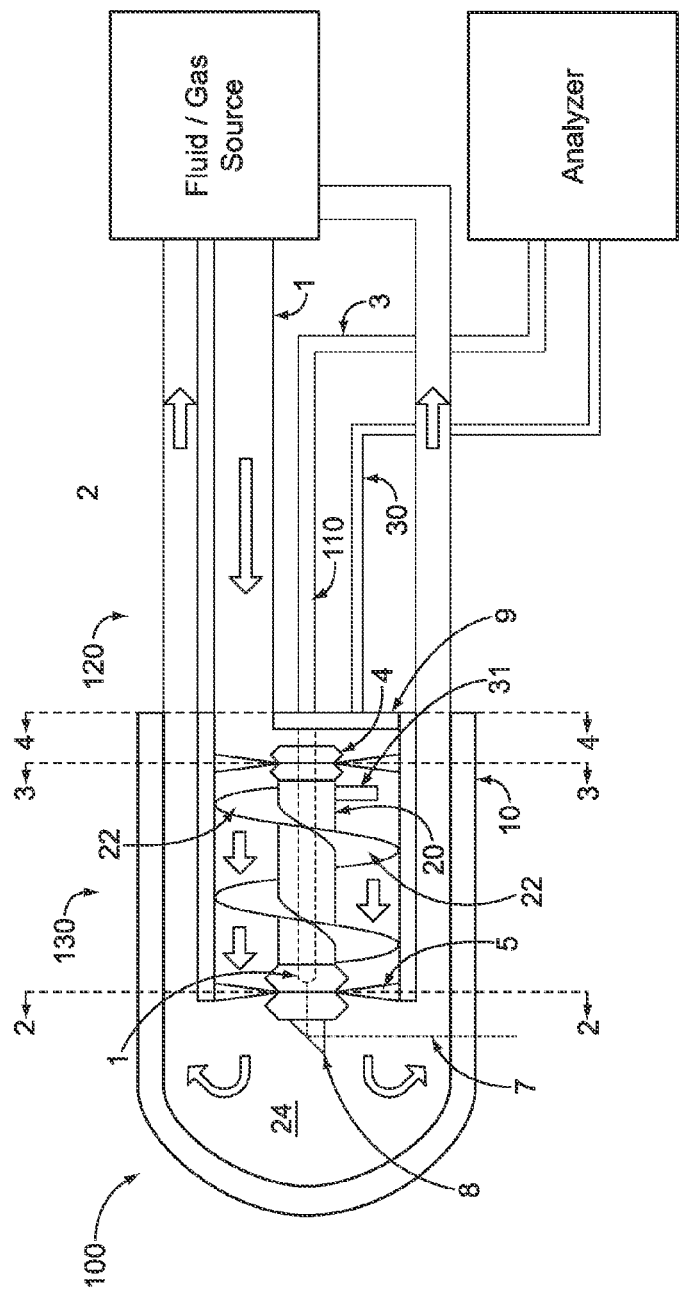
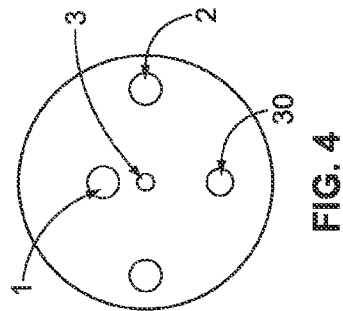
FIG. 1
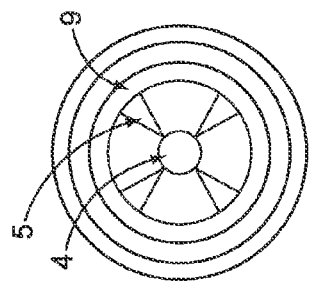
FIG. 2
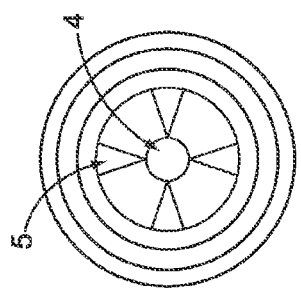
FIG. 3
FIG. 4

Electrostatic Force (Exploded View)

Picture From
"Microsystems Technology 7 (2001), pp. 103-106"

CATHETER IMAGING PROBE AND METHOD

CROSS-REFERENCE TO RELATED APPLICATIONS

This application is National Stage Entry of PCT Application Serial No. PCT/US2004/12773, filed Apr. 23, 2004, which claims the priority of U.S. Provisional Application Ser. No. 60/466,215 file Apr. 28. 2003.

FIELD OF THE INVENTION

The present invention relates to optical coherence tomography based on the use of an optical fiber that does not rotate. More specifically, the present invention relates to optical coherence tomography based on the use of an optical fiber that does not rotate that is enclosed in a catheter that has a tip which does rotate to redirect light from the fiber to a surrounding vessel and the light reflected from the vessel back to the optical fiber.

BACKGROUND OF THE INVENTION

Myocardial infarction or heart attack remains the leading cause of death in our society. Unfortunately, most of us can identify a family member or close friend that has suffered from a myocardial infarction. Until recently many investigators believed that coronary arteries critically blocked with atherosclerotic plaque that subsequently progressed to total occlusion was the primary mechanism for myocardial infarction. Recent evidence from many investigational studies, however, clearly indicate that most infarctions are due to sudden rupture of non-critically stenosed coronary arteries due to sudden plaque rupture. For example, Little and coworkers (Little, W C, Downes, T R, Applegate, R J. The underlying coronary lesion in myocardial infarction: implications for coronary angiography. *Clin Cardiol* 1991; 14: 868-874, incorporated by reference herein) observed that approximately 70% of patients suffering from an acute plaque rupture were initiated on plaques that were less than 50% occluded as revealed by previous coronary angiography. This and similar observations have been confirmed by other investigators (Nissen, S. Coronary angiography and intravascular ultrasound. *Am J Cardiol* 2001; 87 (suppl): 15A-20A, incorporated by reference herein).

The development of technologies to identify these unstable plaques holds the potential to decrease substantially the incidence of acute coronary syndromes that often lead to premature death. Unfortunately, no methods are currently available to the cardiologist that may be applied to specify which coronary plaques are vulnerable and thus prone to rupture. Although treadmill testing has been used for decades to identify patients at greater cardiovascular risk, this approach does not have the specificity to differentiate between stable and vulnerable plaques that are prone to rupture and frequently result in myocardial infarction. Inasmuch as a great deal of information exists regarding the pathology of unstable plaques (determined at autopsy) technologies based upon identifying the well described pathologic appearance of the vulnerable plaque offers a promising long term strategy to solve this problem.

The unstable plaque was first identified and characterized by pathologists in the early 1980's. Davis and coworkers noted that with the reconstruction of serial histological sections in patients with acute myocardial infarctions associated with death, a rupture or fissuring of atheromatous plaque was evident (Davis M J, Thomas A C. Plaque fissuring: the cause of acute myocardial infarction, sudden death, and crescendo angina. *Br Heart J* 1985; 53: 363-373, incorporated by reference herein). Ulcerated plaques were further characterized as having a thin fibrous cap, increased macrophages with decreased smooth muscle cells and an increased lipid core when compared to non-ulcerated atherosclerotic plaques in human aortas (Davis M J, Richardson P D, Woolf N, Katz D R, Mann J. Risk of thrombosis in human atherosclerotic plaques: role of extracellular lipid, macrophage, and smooth muscle cell content, incorporated by reference herein). Furthermore, no correlation in size of lipid pool and percent stenosis was observed when imaging by coronary angiography. In fact, most cardiologists agree that unstable plaques progress to more stenotic yet stable plaques through progression via rupture with the formation of a mural thrombus and plaque remodeling, but without complete luminal occlusion (Topol E J, Rabbaic R. Strategies to achieve coronary arterial plaque stabilization. *Cardiovasc Res* 1999; 41: 402-417, incorporated by reference herein). Neo-vascularization with intra-plaque hemorrhage may also play a role in this progression from small lesions (<50% occluded) to larger significant plaques. Yet, if the unique features of unstable plaque could be recognized by the cardiologist and then stabilized, a dramatic decrease may be realized in both acute myocardial infarction and unstable angina syndromes, and in the sudden progression of coronary artery disease.

The present invention uses depth-resolved light reflection or Optical Coherence Tomography (OCT) to identify the pathological features that have been identified in the vulnerable plaque. In OCT, light from a broad band light source is split by an optical fiber splitter with one fiber directing light to the vessel wall and the other fiber directing light to a moving reference mirror. The distal end of the optical fiber is interfaced with a catheter for interrogation of the coronary artery during a heart catheterization procedure. The reflected light from the plaque is recombined with the signal from the reference mirror forming interference fringes (measured by a photovoltaic detector) allowing precise depth-resolved imaging of the plaque on a micron scale.

OCT uses a superluminescent diode source emitting a 1300 nm wave length, with a 50 nm band width (distribution of wave length) to make in situ tomographic images with axial resolution of 10-20 µm and tissue penetration of 2-3 mm. OCT has the potential to image tissues at the level of a single cell. In fact, the inventors have recently utilized broader band width optical sources such as femto-second pulsed lasers, so that axial resolution is improved to 4 µm or less. With such resolution, OCT can be applied to visualize intimal caps, their thickness, and details of structure including fissures, the size and extent of the underlying lipid pool and the presence of inflammatory cells. Moreover, near infrared light sources used in OCT instrumentation can penetrate into heavily calcified tissue regions characteristic of advanced coronary artery disease. With cellular resolution, application of OCT may be used to identify other details of the vulnerable plaque such as infiltration of monocytes and macrophages. In short, application of OCT can provide detailed images of a pathologic specimen without cutting or disturbing the tissue.

One concern regarding application of this technology to image atherosclerotic plaques within the arterial lumen is the strong scattering of light due to the presence of red blood cells. Once a catheter system is positioned in a coronary artery, the blood flow between the OCT optical fiber and artery can obscure light penetration into the vessel wall. One proposed solution is the use of saline flushes. Saline use is limited in duration, however, since myocardial ischemia eventually occurs in the distal myocardium. The inventors have proposed the use of artificial hemoglobin in the place of saline. Artificial hemoglobin is non-particulate and therefore does not scatter light. Moreover, artificial hemoglobin is about to be approved by the United States Food and Drug Administration as a blood substitute and can carry oxygen necessary to prevent myocardial ischemia. Recently, the inventors demonstrated the viability of using artificial hemoglobin to reduce light scattering by blood in mouse myocardium coronary arteries (Villard J W, Feldman M D, Kim Jeehyun, Milner T E, Freeman G L. Use of a blood substitute to determine instantaneous murine right ventricular thickening with optical coherence tomography. *Circulation* 2002; Volume 105: Pages 1843-1849, incorporated by reference herein).

The first prototype of an OCT catheter to image coronary plaques has been built and is currently being tested by investigators in Boston at Harvard—MIT (Jang I K, Bouma B E, Kang D H, et al. Visualization of coronary atherosclerotic plaques in patients using optical coherence tomography: comparison with intravascular ultrasound. *JACC* 2002; 39: 604-609, incorporated by reference herein) in association with Light Lab Co. The prototype catheter consists of a single light source and is able to image over a 360 degree arc of a coronary arterial lumen by rotating a shaft that spins the optical fiber. Because the rotating shaft is housed outside of the body, the spinning rod in the catheter must rotate with uniform angular velocity so that the light can be focused for equal intervals of time on each angular segment of the coronary artery. Mechanical drag in the rotating shaft can produce significant distortion and artifacts in recorded OCT images of the coronary artery. Unfortunately, because the catheter will always be forced to make several bends between the entry point in the femoral artery to the coronary artery (e.g., the 180 degree turn around the aortic arch), uneven mechanical drag will result in OCT image artifacts As the application of OCT is shifted from imaging gross anatomical structures of the coronary artery to its capability to image at the level of a single cell, non-uniform rotation of the single fiber OCT prototype will become an increasingly problematic source of distortion and image artifact.

Essentially, current endoscope type single channel OCT systems developed by Light Lab Co. suffers by non-constant rotating speed that forms irregular images of a vessel target. See U.S. Pat. No. 6,134,003, incorporated by reference herein. Their approach of a rotary shaft to spin a single mode fiber is prone to produce artifact. The catheter will always be forced to make several bends from its entry in the femoral artery, to the 180 degree turn around the aortic arch, to its final destination in the coronary artery. All these bends will cause uneven friction on the rotary shaft, and uneven time distribution of the light on the entire 360 degree arch of the coronary artery. As the application of OCT is shifted from gross anatomical structures of the coronary artery to its capability to image at the level of a single cell, then non-uniform rotation of the single fiber OCT will become even a greater source of greater artifact.

The present invention overcomes this disadvantage of current single mode endoscope OCT by putting a rotating part at the end of the fiber probe. The rotating part is driven by biocompatible gas or liquid pumped externally. The rotating part is based on a miniature turbine, screw or water wheel, or nanotechnology. The single mode fiber itself will not be turned at all, but only a prism reflecting incident light to the target vessel wall will rotate at constant speed.

SUMMARY OF THE INVENTION

The present invention pertains to a catheter imaging probe for a patient. The probe comprises a conduit through which energy is transmitted. The probe comprises a first portion through which the conduit extends. The probe comprises a second portion which rotates relative to the conduit to redirect the energy from the conduit.

The present invention pertains to a method for imaging a patient. The method comprises the steps of inserting a catheter into the patient. There is the step of rotating a second portion of the catheter relative to a conduit extending through a first portion of the catheter, which redirects the energy transmitted through the conduit to the patient and receives the energy reflected back to the second portion from the patient and redirects the reflected energy to the conduit.

BRIEF DESCRIPTION OF THE DRAWINGS

In the accompanying drawings, the preferred embodiment of the invention and preferred methods of practicing the invention are illustrated in which:

FIG. 1 is a schematic representation of the present invention.

FIG. 2 is a cross-section of 2-2 of FIG. 1.

FIG. 3 is a cross-section of 3-3 of FIG. 1.

FIG. 4 is a cross-section of 4-4 of FIG. 1.

DETAILED DESCRIPTION

Figure 5:
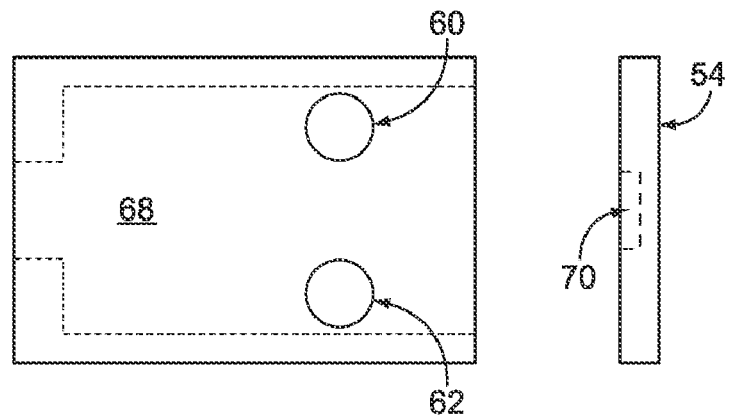
FIG. 5 is a schematic representation of a capsule.
Figure 6:
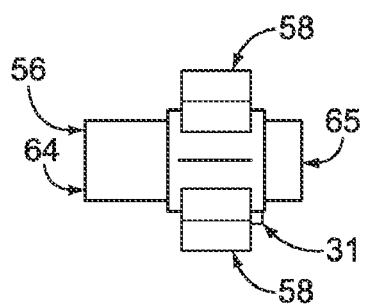
FIG. 6 is a schematic representation of a side view of a wheel.
Figure 7:
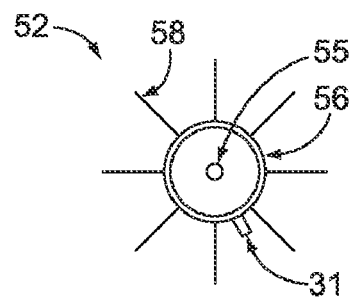
FIG. 7 is a schematic representation of an axial view of the wheel.
Figure 8:
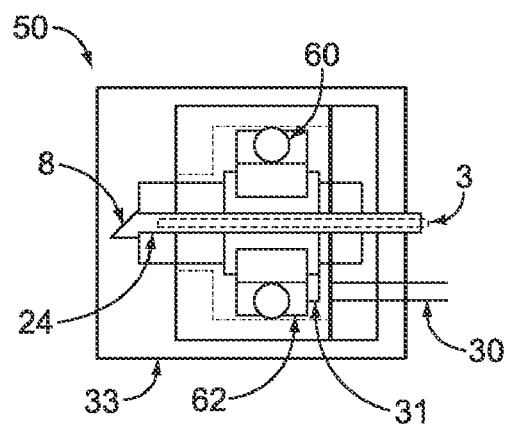
FIG. 8 is a schematic representation of a side view of the mill.
Figure 9:
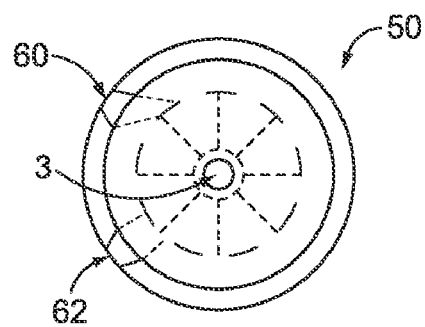
FIG. 9 is a schematic representation of an axial view of the mill.

Referring now to the drawings wherein like reference numerals refer to similar or identical parts throughout the several views, and more specifically to FIG. 1 thereof, there is shown a catheter imaging probe 100 for a patient. The probe 100 comprises a conduit 110 through which energy is transmitted. The probe 100 comprises a first portion 120 through which the conduit 110 extends. The probe 100 comprises a second portion 130 which rotates relative to the conduit 110 to redirect the energy from the conduit 110.

Preferably, the first portion 120 includes an inlet tube 1 through which fluid flows and wherein the second portion 130 is turned by flowing fluid from the inlet tube 1. The second portion 130 preferably includes a turbine 4 which is turned by the flowing fluid. Preferably, the turbine 4 includes a rotating center shaft 20 through which the conduit 110 extends, and spiral shaped inner grooves 22 which extend from the center shaft 20 that provide a rotating torque to the center shaft 20 when the flowing fluid flows against the grooves 22 that causes the center shaft 20 to rotate about the conduit 110.

The second portion 130 preferably has a reflecting material 24 attached to the center shaft 20 which redirects the energy from the conduit 110. Preferably, the conduit 110 includes an optical fiber 3. The reflecting material 24 preferably includes a prism 8 or a mirror which reflects light from the conduit 110, the prism 8 rotating with the center shaft 20. Preferably, the turbine 4 includes knobs 5 which support the center shaft 20 which allows the shaft to rotate without wobbling. The first conduit 110 preferably includes at least one outlet tube 2 through which fluid flows from the second portion 130.

Preferably, the second portion 130 includes a cover 10 transparent to the energy which encapsulates the cylinder and contacts the first portion 120 so no fluid can escape from the second portion 130 except through the outlet tube 2. The second portion 130 preferably includes a cylinder attached to the first portion 120 from which the knobs 5 extend and that defines a chamber which fluid from the inlet tube 1 flows through. The turbine 4 is disposed in the chamber. Preferably, the second portion 130 includes an energy field reshaping component, such as a lens 11, which focuses the energy onto the patient. The lens 11 can be a microlens, grin lens, or optical fiber lens. The probe 100 preferably includes a fluid source 26 connected to the inlet tube 1. Preferably, the fluid in the fluid source 26 is chosen from the group consisting of nitrogen, helium, saline, water, D5W or artificial blood. The first portion 120 is solid except for the conduit 110 and the inlet and outlet tubes 1, 2.

Preferably, the turbine 4 includes a wart 31 which reflects energy coming through a radiation energy guide 30 back to the radiation energy guide 30 (another optical fiber preferably). The wart 31 rotates with the second portion 130. The energy reflected by the wart 31 indicates current angular position of the second portion 130. The wart 31 identifies one angular position (not all the positions) of the rotating portion when the light hits and gets back from the wart 31. In this way, it is known the shaft 20 rotates one cycle and also the starting position of the acquired image on the vessel wall. The wart 31 is preferably a block shape with a flat wall facing the radiation energy guide 30, to reflect the energy back. It is preferably molded into the shaft 20, and the flat wall can have a reflective material, such as a mirror placed on it to increase the reflection. The width of the wart is small compared to the circumference of the shaft 20, so as to identify a given point, and is high enough to block the energy emitted from radiation energy guide 30, so it is reflected by the wart 31.

The present invention pertains to a method for imaging a patient. The method comprises the steps of inserting a catheter into the patient. There is the step of rotating a second portion 130 of the catheter relative to a conduit 110 extending through a first portion 120 of the catheter, which redirects the energy transmitted through the conduit 110 to the patient and receives the energy reflected back to the second portion 130 from the patient and redirects the reflected energy to the conduit 110.

Preferably, the rotating step includes the step of flowing fluid through an inlet tube 1 to the second portion 130 to turn the second portion 130. The following step preferably includes the step of flowing fluid through the inlet tube 1 to turn a turbine 4 of the second portion 130. Preferably, the flowing step includes the step of flowing the fluid against spiral shaped inner grooves 22 which extend from a rotating center shaft 20 of the turbine 4 to create a rotating torque on the center shaft 20 that causes the center shaft 20 to rotate about the conduit 110 that extends through the center shaft 20. The second portion 130 preferably has a reflecting material 24 attached to the center shaft 20 which redirects the energy from the conduit 110. Preferably, the conduit 110 is an optical fiber 3.

The reflecting material 24 preferably includes a prism 8 or mirror which reflects light from the conduit 110, and including the step of rotating the prism 8 with the center shaft 20 as the center shaft 20 is rotated by the flowing fluid. Preferably, the rotating step includes the step of rotating the center shaft 20 that is supported by knobs 5 of a cylinder of the turbine 4 in which the center shaft 20 is disposed. The flowing step preferably includes the step of flowing the fluid from the inlet tube 1 through the chamber of the cylinder. Preferably, the flowing step includes the step of removing the fluid flowing from the cylinder of the second portion 130 through at least one outlet tube 2 that extends through the first portion 120.

In the operation of the invention, FIG. 1 shows the diagram of turbine 4 based catheter type imaging probe 100 which may be connected to sample arm of single mode fiber 3 OCT. FIGS. 2, 3 and 4 are cross-sectional images of the probe 100 at cross-section (2), (3), (4). At the center of the probe 100, there is a turbine 4 which is connected to a prism 8. Gas or liquid flows through an outlet tube 2 into the turbine 4 chamber. The turbine 4 is supported by knobs 5 to maintain constant position during rotation. At the center of the turbine 4, there is a hole to place an optical fiber 3 that is glued onto a cylinder 9. During the rotation of the turbine 4, the optical fiber 3 will not move or rotate at all. All of these parts are capsulated by outmost transparent cover 10. The material for this transparent cover can be any biocompatible polymers (e.g. plastic Tygon). Probing light will be launched from the single mode optical fiber 3 through a lens 11 having a curvature to focus the light onto target tissue area. A rotating prism 8 connected to the turbine 4 reflects incoming light toward target tissue area on the vessel wall. The reflected light from the target tissue goes back into the fiber 3 through the prism 8. A standard analysis on the light is then performed to obtain the image. See U.S. Pat. No. 6,134,003, incorporated by reference herein. Gas or liquid gone through the turbine 4 exits the probe 100 through an outlet tube 2. Rotation direction and speed of the second portion are controlled by the pressure difference between the inlet 1 and outlet 2.

Applying gas or liquid through an inlet tube 1 pressure is induced to the turbine 4 which rotates; therefore, a prism 8 put on the end of the turbine 4 rotates too. Finally, an imaging system can scan 360 degree around the inner vessel wall at constant speed.

Preferred Materials
- Gas: Nitrogen, Helium, $CO_2$ or any gas that can be dissolved into blood or tissue relatively easily.
- Fluid: Saline, D5W, or artificial blood (Oxyglobin)
- Turbine 4: Stainless steel, plastic Tygon or Teflon
- Cylinder 9: Teflon
- Cover 10: Plastic Tygon or any biocompatible transparent plastic Preferred Dimensions
- Outer diameter of transparent cover 10: 1.2 mm
- Outer diameter of cylinder 9: 0.8 mm
- Outer diameter of inlet tube 1: 0.2 mm Outer diameter of outlet tube 2: 0.2 mm
Outer diameter of fiber 3: 0.1125 mm Preferred Characteristics
Target speed: 720 degree/sec
Turbine length: 0.5 mm
Turbine pitch: 4 pitch/mm
Speed of gas flow: 0.5 mm/sec
Turbine area: $0.35^2*pi=0.38$ mm$^2$
Volume of the inner cylinder for the turbine: $0.38*0.5=0.19$ mm$^3$
Target flow rate: 0.19 mm$^3$/sec The above are all examples. The invention is not limited to these values. For instance, to obtain a finer image, the flow rate is lower and the time it takes to obtain an image is then longer.

In an alternative preferred embodiment shown in FIGS. 5-9, the second portion 130 includes a mill 50. The mill 50 preferably includes a wheel 52. Preferably, the mill 50 includes a capsule 54 which holds the wheel 52. The conduit 55 is preferably an optical fiber 3. Preferably, the wheel 52 includes a plug 56, and fins 58 which extend radially from the plug 56. The plug 56 has a hole at the center which receives the optical fiber. The fins 58 are pushed by the fluid causing the plug 56 to rotate.

The capsule 54 preferably includes an inlet port 60 and an outlet port 62. Preferably, the second portion 130 has a reflecting material 24 attached to the plug 56 which redirects the energy from the optical fiber 3. The reflecting material 24 preferably includes a prism 8 which reflects light from the optical fiber 3, the prism 8 rotating with the plug 56. Preferably, the capsule 54 includes a first pocket 68 and a second pocket 70, in which a first end 64 of the plug 56 and a second end 66 of the plug 56 are respectfully disposed, the first and second pockets 68, 70 maintaining the plug 56 in position in the capsule 54 as the plug 56 rotates.

The second portion 130 preferably includes a cover 33 transparent to the energy which encapsulates the capsule 54 and contacts or attaches to the first portion 120 so no fluid can escape from the second portion 130 except through the outlet tube 2. The cover 333 can be glued to the first portion. Alternatively, the cover 33 can be of a long enough length that it extends the length of the first portion and the second portion. During assembly, after the mill (or for that matter the turbine) is connected to the first portion, then the mill and the first portion are inserted into the cover, which is basically a long hollow transparent tube with a closed end. The mill on the end of the first portion is then fed through the tube until it is in place at the end of the tube. The flexible tube can be of such an inner diameter that it forms a tight fit with the outer circumference of the first portion and prevents fluid from escaping the end about the mill except through the outlet port.

The probe 100 preferably includes a fluid source 26 connected to the inlet tube 1. Preferably, the fluid in the fluid source 26 is chosen from the group consisting of nitrogen, helium, $CO_2$, saline, water, D5W, ringers lactate or artificial blood.

Preferably, the plug 56 includes a wart 31 which reflects energy coming through a radiation energy guide 30 back to the radiation wave guide 30. The wart 31 rotates with the plug 56. The energy reflected by the wart 31 indicates current angular position of the second portion 130.

Preferably, the following step includes the step of flowing fluid through the inlet tube 1 to turn a wheel 52 of a mill 50 of the second portion 130. The flowing step preferably includes the step of flowing the fluid against fins 58 which extend from a rotating plug 56 of the wheel 52 to cause the wheel 52 to rotate about the conduit 55 that extends through the plug 56. Preferably, the second portion 130 has a reflecting material 24 attached to the plug 56 which redirects the energy from the conduit 55. The conduit 55 preferably is an optical fiber 3. Preferably, the reflecting material 24 includes a prism 8 which reflects light from the conduit 55, and including the step of rotating the prism 8 with the plug 56 as the wheel 52 is rotated by the flowing fluid. Rotating direction and speed of the second portion are controlled by the pressure difference between the inlet and outlet 60, 62.

The rotating step preferably includes the step of rotating the wheel 52 that is disposed in pockets of a capsule 54 of the mill 50 in which the wheel 52 is disposed. Preferably, the flowing step includes the step of flowing the fluid from the inlet tube 1 through an inlet port 60 of the capsule 54 into the capsule 54. The flowing step preferably includes the step of removing the fluid flowing from an outlet port 62 of the capsule 54 of the second portion 130 through at least one outlet tube 2 that extends through the first portion 120 so a rotational flow path is created with the fluid through the capsule 54 which rotates the wheel 52 as the fluid flows against the fins 58.

In the operation of the alternative preferred embodiment, and referring to FIGS. 5-9, the probe 100 is introduced into the patient through the femoral artery, as is well known in the art, and moved to a desired location in regard to the heart by standard catheterization techniques. Once the probe 100 is at the desired location, a gas, such as nitrogen, $CO_2$ or helium or any gas that can be dissolved into tissue relatively easily or a liquid, such as saline, D5W, lactated ringers or artificial blood (oxyglobin), is introduced from the fluid source 26 to the inlet tube 1 in the first portion 120 of the probe 100. The first portion 120 of the probe 100 is essentially solid except for the inlet tube 1, and an outlet tube 2 and the optical fiber 3, which extend through the first portion 120.

The second portion 130 of the probe 100 is attached, such as by being glued, to the first portion 120. When the second portion 130 is attached to the first portion 120, it is aligned properly with the first portion 120 so the optical fiber 3 extends from the first portion 120 into the center of the second portion 130 along its axis that is hollow to receive the optical fiber 3. In addition, the inlet tube 1 aligns with an inlet port 60 of the second portion 130, and the outlet tube 2 aligns with the outlet port 62 of the second portion 130 so fluid from the inlet tube 1 flows into the inlet port 60, and fluid from the outlet port 62 flows into the outlet tube 2. Both the inlet port 60 and the outlet port 62 have bends in them to redirect the direction of flow of the fluid flowing along the axial direction in the inlet tube 1 towards a generally radial direction into the second portion 130, and generally from a radially outward direction from the second portion 130 into an axial direction down the outlet tube 2, respectively. Rotating direction and speed of the second portion are controlled by the pressure difference between the inlet and outlet 60, 62.

The second portion 130 is in the form of a mill 50 with a wheel 52 disposed in a capsule 54. The wheel 52 comprises a plug 56 having a hollow central axis through which the optical fiber 3 extends, and fins 58 that extend radially outward from the plug 56. A first end 64 of the plug 56 is disposed in a first pocket 68 of the capsule 54, and a second end 65 of the plug 56 is disposed in a second pocket 70 of the capsule 54. The first and second pockets 68, 70 maintain the plug 56 in a desired location in the capsule 54, while allowing the plug 56 to freely rotate inside the capsule 54. The plug 56 with the fins 58 is introduced to the capsule 54 by a cap of the capsule 54 being removed so the plug 56 can be introduced into the body of the capsule 54. The end of the cap is then fitted back on the body with the first end 64 of the plug 56 disposed in the first pocket 68 and the second end 66 of the plug 56 disposed in the second pocket 70 that is found in the cap.

As fluid flows through the inlet tube 1 to the outlet port 62 and into the capsule 54, it strikes the fins 58 and causes the fins 58 to move under the force of the fluid flow. This movement of the fins 58 effectively causes the plug 56 to rotate. The fluid flows against the fins 58 from the inlet port 60 and follows a path about the plug 56 as it rotates and then out the capsule 54 at the outlet port 62 to complete its traverse of the interior of the capsule 54. The fluid leaves the interior of the capsule 54 through the outlet port 62 and then is carried away from the capsule 54 through the outlet tube 2 and ultimately out of the body of the patient. A rotational fluid path is effectively created to maintain the plug 56 in rotation by the fluid entering the capsule 54 through the inlet port 60 at a point above the plug 56 relative to the outlet port 62 that is disposed below the plug 56. Rotating direction and speed of the second portion are controlled by the pressure difference between the inlet and outlet 60, 62.

When the plug 56 rotates, a prism 8 disposed at the first end 64 is in alignment with the central axis of the plug 56, and thus the central axis of the optical fiber 3, and rotates at the same speed as plug 56. The optical fiber 3, which is disposed in the center of plug 56 is essentially out of contact with plug 56, and stays still as the plug 56 rotates about it due to the action of the fluid turning the fins 58. The light emitted from the optical fiber 3 is redirected by the prism 8 radially outwards towards the interior wall of the vessel in which the probe 100 is disposed. The rotation of the prism 8 causes the light to be scanned across a continuous arc, around and around across the circumference of the interior wall of the vessel. A cover 33 covers the capsule 54 and protects the capsule 54 from the environment inside the vessel, such as from blood or other fluids or particles. The cover 33 is transparent to allow the light emitted from the optical fiber 3 to pass through it and strike the vessel, and from light reflected by the interior of the vessel to pass back through the cover 33 towards the prism 8, where it is once again redirected this time into the optical fiber 3 from whence it once came. The reflected light, however, now carries with it information about the properties of the vessel that have caused changes in the light and manifested in the reflected light that is transmitted back along the optical fiber 3 and outside the patient to an analyzer. The analyzer then uses well known techniques to analyze the reflected light that it has received.

The mill 50 and the fins 58 are, for example, made of stainless steel, Mg alloy, plastic, Tygon or Teflon. The capsule 54 is, for instance, made of Teflon. The cover 33 is, for instance, made of plastic Tygon or any biocompatible transparent plastic. The outer diameter of the probe 100 is approximately 1 mm. The approximate tip length of the second portion 130 of the probe 100 is 5 mm. A target rotating speed for the wheel 52 is about 720 degrees per second, with a target flow rate of about 0.19 mm³ per second of fluid flowing through the capsule 54.

Figure 10A:
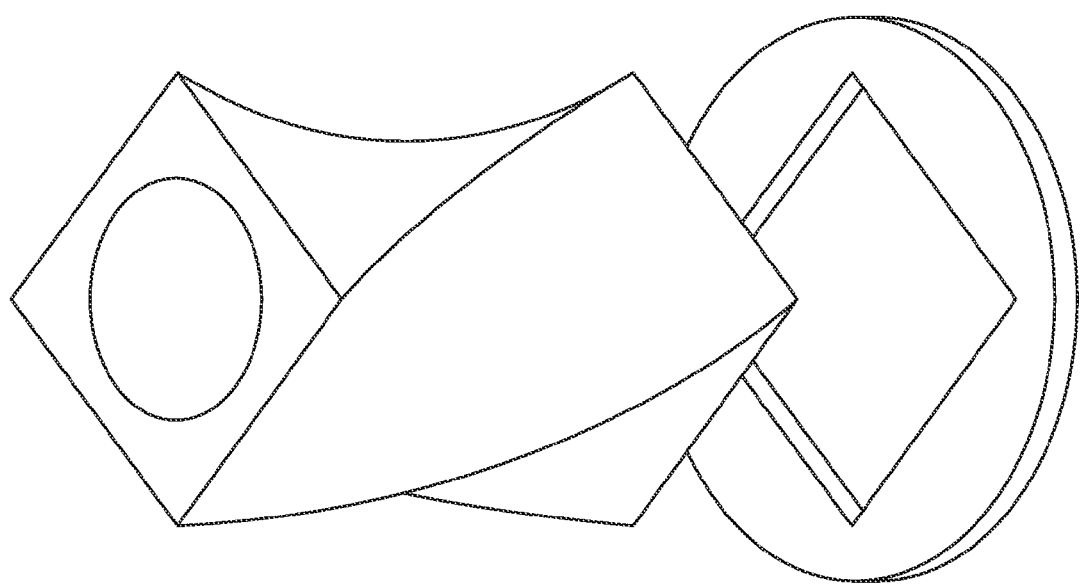
FIGS. 10a and 10b are schematic representations of a screw embodiment.
Figure 10B:
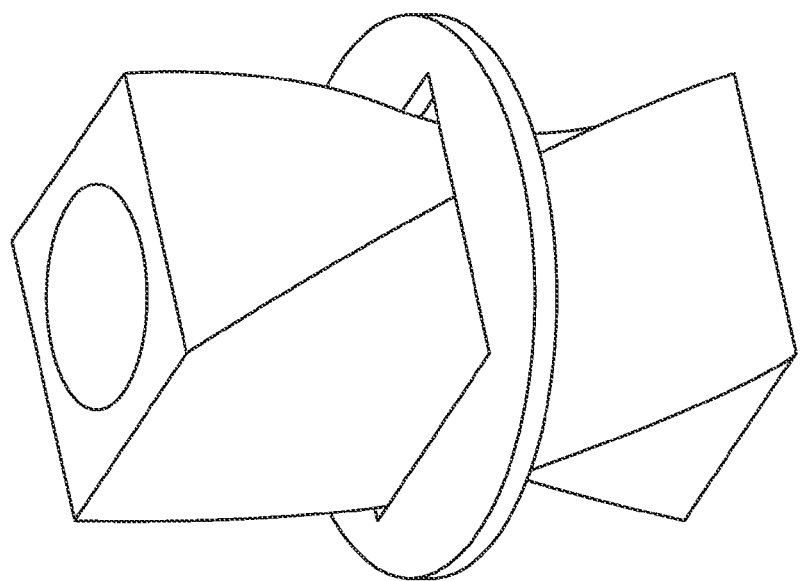

As shown in FIGS. 10a and 10b, a screw embodiment can also be used, with fluid flow direction moving the screw forward or back depending on the direction of the fluid flow.

Figure 17:
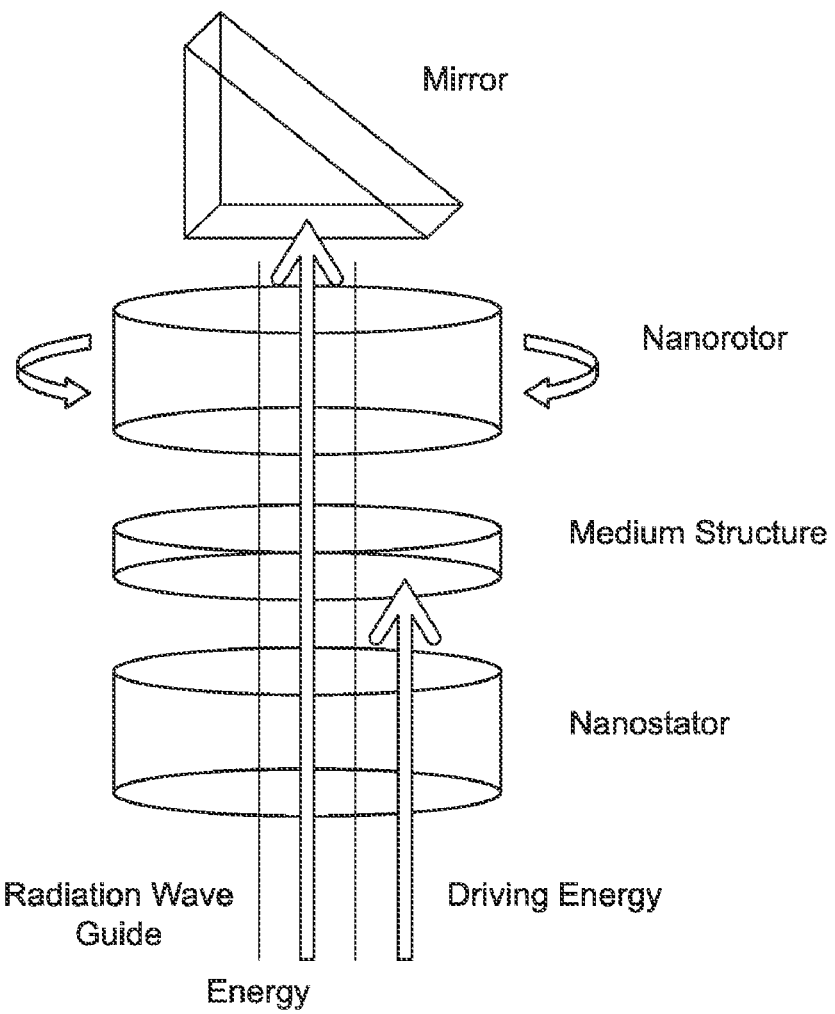
FIG. 17 is a schematic representation of a nanorotor-nanostator embodiment generally.

See FIG. 17 for reference to the following descriptions regarding different embodiments of nanotechnology based probe tips.

Figure 11:
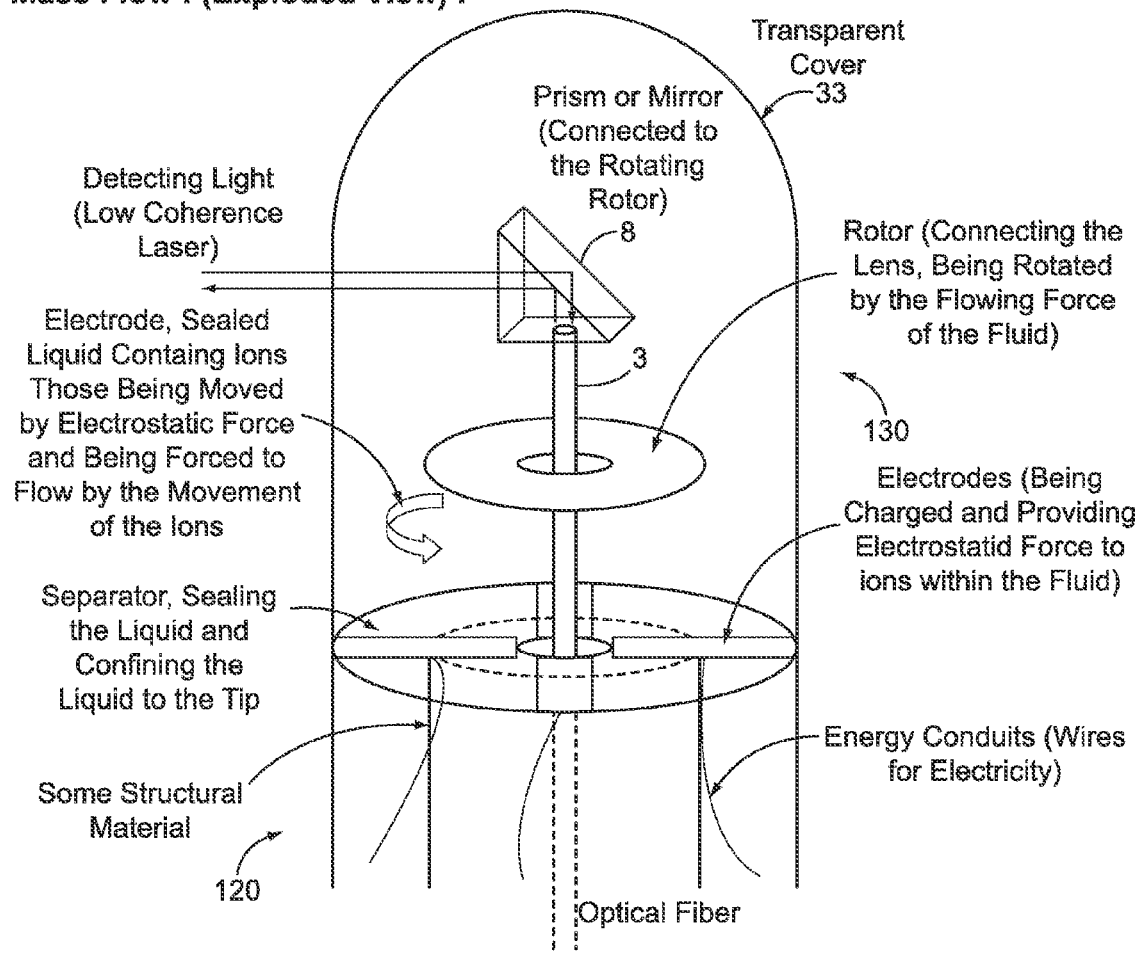
FIG. 11 is a schematic representation of an exploded view of a mass flow embodiment.

Mass Flow:

If the media is a solution, a mass flow can be generated in the solution to provide the torque actuating the rotor, as shown in FIG. 11. The flow-actuated turbine that is desirable above is one example. In that case, the mass flow is the flow of the flowing fluid.

Figure 12:
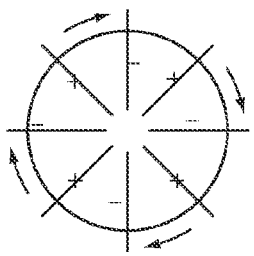
FIG. 12 is a schematic representation of electric field direction.

Mass flow could be ions flow. When the media is a kind of electrolyte, such as NaCl solution, an electric field can be provided to make the ions, such as $Na^+$ and $Cl^-$, move toward opposite directions. The mass flow generated from the movement of the ions would provide a net momentum that make the solvent, that is, the water flow. An electric field that surrounds the shaft of the nanomotor makes it strong enough to affect the media electrolyte between the stator and the rotor, the water in the media electrolyte will flow around the shaft such that a torque will be generated between the stator and the rotor. Furthermore, with obstacle structures, such as fans, on the rotor, the torque will be more sufficiently used. The circular-oriented electric field can be provided by interlacing electrodes for positive and negative charge, as shown in FIG. 12, around the media area.

Figure 13:
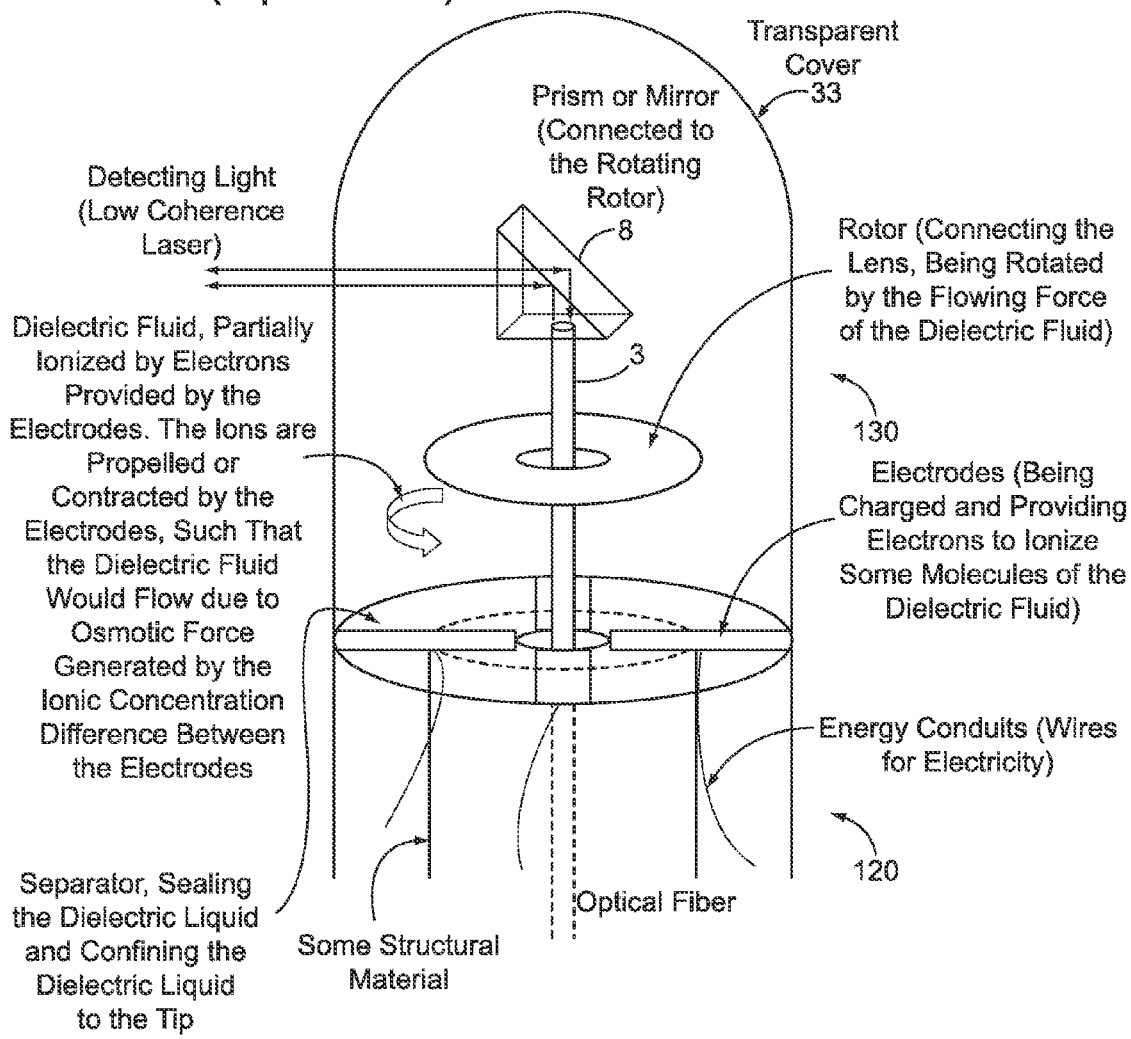
FIG. 13 is a schematic representation of an exploded view of another mass flow embodiment.

Mass flow induced by osmotic force is another choice, as shown in FIG. 13. Osmotic force is generated when there is a density difference between any two areas in one solution. The solvent would tend to flow toward the area of the higher solute density. Some people had invented a method to use this phenomenon. In their devices, although very similar to the above example about electrolyte case, they used dielectric fluid as the media, and they used strongly charged electrodes to provide free electrons moving between electrodes such that the electrons would ionize some molecules of the dielectric fluid. The molecule ions tended to move to negatively charged electrode and created the density difference required for the generation of the osmotic force. This kind of actuation is also named ion-drag actuator.

Material's Deformation

Figures 14A, 14B:
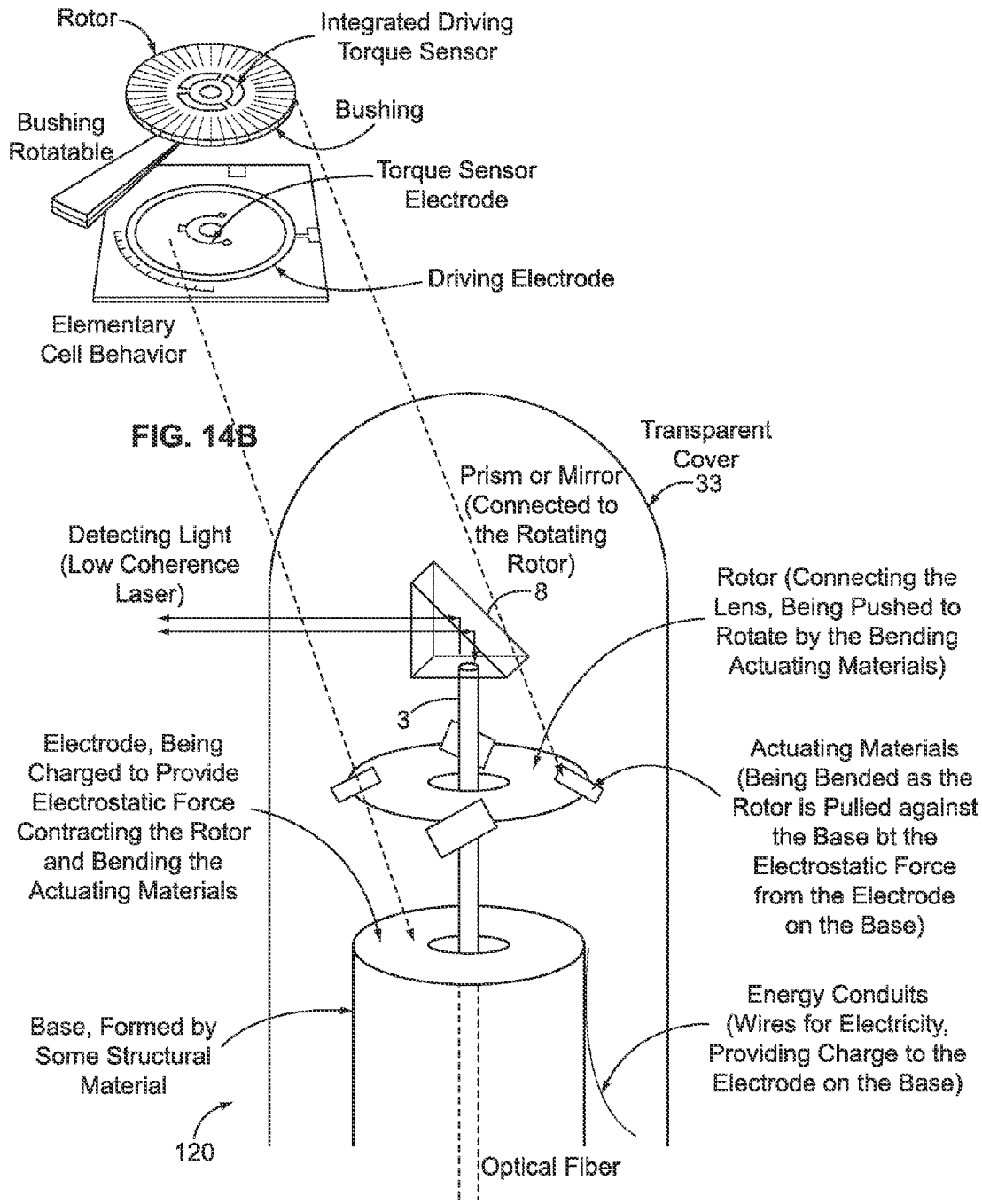
FIGS. 14a and 14b are schematic representations of an exploded view of deformable material as the media.

When the media is a solid material, a torque can be generated between the stator and the rotor by periodically generating the deformation in the media material. Imagine how some caterpillars move without walking by foot. They typically bend and stretch their bodies periodically, such that they can receive movement by means of frictions between their skins and the sticks on trees. The nanomotor can work in the same way. Like the electrolyte example above, a circular-oriented "bend and stretch" structure can be made to generate torque about the shaft. In this case, the media material can be only connected to the rotor, only connected to the stator, or connected to none of them. An example is shown in FIGS. 14a and 14b, where FIG. 14b is a detailed view of the rotor and the electrode.

The term "periodical" implies vibration. The structure is not necessarily in the "caterpillar" form, but a disk-shaped material can be used that can be vibrated like a Pizza turning on the cooker's fingertip. Just like a cell phone ringing in vibration mode, it moves or even rotates on the table. Generally, periodical deformation (or vibration) and friction can generate movement, and the rotation motion we need is a special case of the movement.

There are several ways the deformation in the material can be achieved. The first is adjusting temperature to change the atomic lattice structure, named "phase", of the material. Shape memory alloy (SMA) is a good example. Decades of degree's temperature raise can make a properly designed SMA structure generating a big geometrical change.

Figure 15:
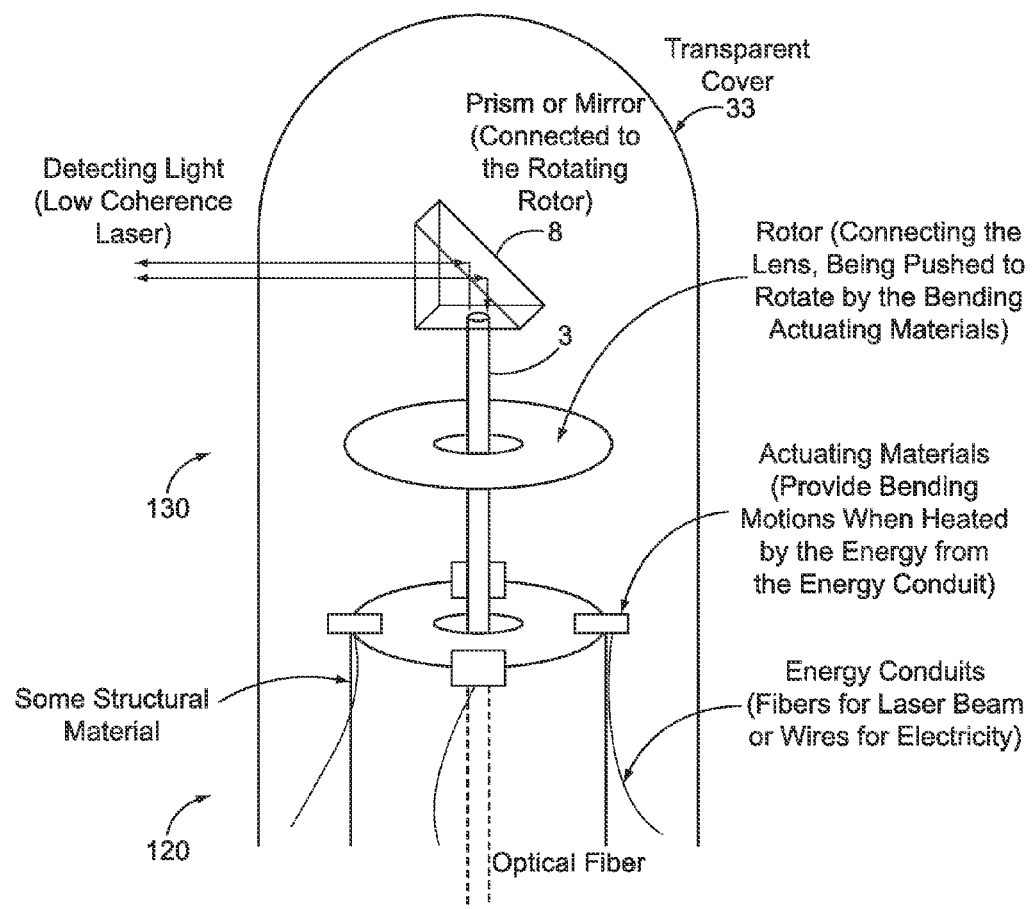
FIG. 15 is a schematic representation of an exploded view of another deformable material embodiment.
Figure 16B:
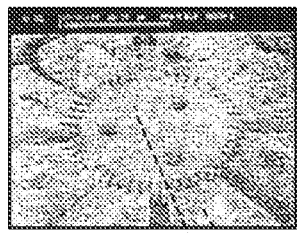
FIGS. 16a and 16b are schematic representations of an electrostatic force embodiment.
Figure 16A:
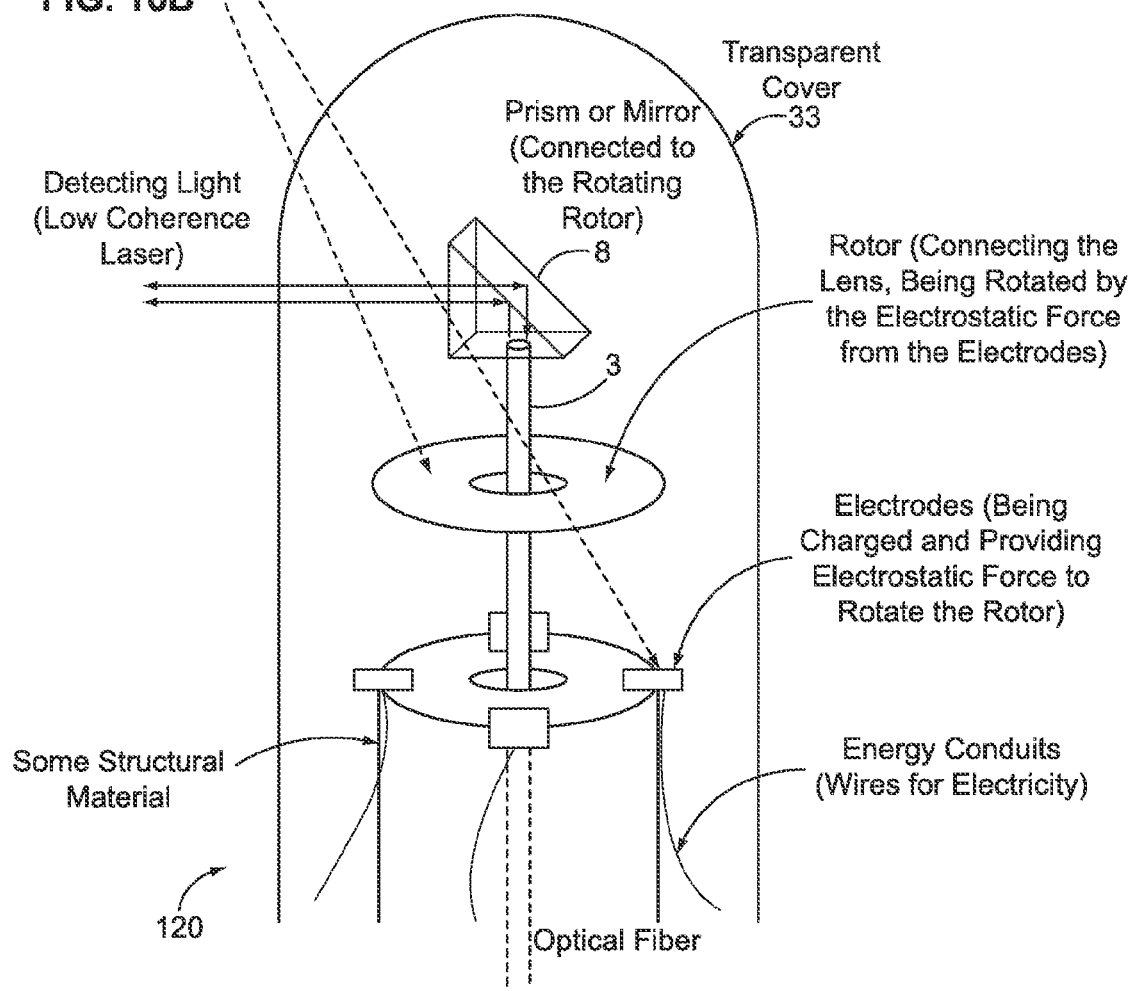

The second one is thermal expansion or contraction, which is a similar concept like that of the first one, as shown in FIG. 15. The third, in addition to heat energy, electric field can be used to contract a dielectric media material to generate deformation, such as bending. Finally, electric voltage can be directly applied to the media when piezoelectric material is used as the media material. Piezoelectric material can generate high deformation and high force and is widely applied in ultrasonic motors, in which an electric wave of high frequency is used to actuate a piezoelectric structure disposed between the rotor and the stator (In most cases, the rotor itself is the piezoelectric structure). See FIGS. 16*a* and 16*b*, where FIG. 16*b* is a detailed view of the rotor and the electrodes.

In most cases, the rotor is combined with the media structure. The rotor has teeth formed around it. For instance, in a triangular shape, which allows the rotor to slide along the slope of the hypotenuse in one direction but not move back against the vertical edge. The stator is further comprised of a plurality of electrodes surrounding the rotor without contact. In operation, the electrodes are charged interchangingly, such to generate induced charge on the teeth of the rotor. The attracting force between the teeth and the electrodes then generates a torque.

Generally, additional applications for the probe 100 include:

(1) GI tract. Colonoscopy and Endoscopy both currently can only exam the surface of the GI tract. When suspicious areas that may represent cancer are identified, a biopsy is required. OCT has the advantage of visualizing 2-4 mm into the wall of the GI tract and has resolution to the level of a single cell. The probe can provide histologic images without the need to biopsy tissue to visualize and diagnose cancer in real time.

(2) GU tract. Cystoscopy is a method to visualize the bladder with a light source to aid in the diagnosis of transitional cell cancer of the inner surface of the bladder wall. Application of cystoscopy requires a biopsy to make the final diagnosis of transitional cell cancer. The probe 100 can penetrate several millimeters into the bladder wall, visualize at the single cell level, and make a diagnosis of transitional cell cancer without removing tissue.

(3) Cervical and uterine cancer. Currently the gold standard for diagnosing cervical cancer is a pap smear, where cells are scraped off the cervix, and examined under a light microscope to diagnose cancer. Similarly, women also have the inner lining of the uterus scraped and examined under a microscope to identify cancer cells. The probe 100 can image dysplastic and malignant lesions and quantify changes in the nucleous.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A catheter imaging probe for a patient comprising: a conduit through which electromagnetic radiation is transmitted; a first portion through which the conduit extends; and a second portion which provides movement relative to the conduit to redirect the electromagnetic radiation from the conduit, the first portion includes an inlet tube through which fluid flows and wherein the second portion is moved by flowing fluid from the inlet tube, wherein the second portion includes a rotor through which the conduit extends and a capsule containing the rotor, the rotor and inner surface of the capsule defines at least one flowing route extending about the rotor and the conduit includes at least one outlet tube through which fluid flows from the second portion, guiding the fluid flowing along the flowing route and causing the rotor to rotate about the conduit via reactive force provided by the fluid.

2. A probe as described in claim 1 wherein the rotor includes a rotating center shaft through which the conduit extends, and spiral shaped inner grooves which extend from the center shaft that provide a rotating torque to the center shaft when the flowing fluid flows against the grooves that causes the center shaft to rotate about the conduit.

3. A probe as described in claim 2 wherein the second portion has one or more optical redirection elements attached to the center shaft which redirects the electromagnetic radiation from the conduit.

4. A probe as described in claim 3 wherein the conduit is a radiation waveguide.

5. A probe as described in claim 4 wherein the radiation waveguide is a single mode fiber.

6. A probe as described in claim 5 wherein the optical redirection element includes a prism which reflects light from the conduit, the prism rotating with the center shaft.

7. A probe as described in claim 6 wherein the capsule includes knobs which support the center shaft which allows the shaft to rotate without wobbling.

8. A probe as described in claim 7 wherein the second portion includes a cover having at least a portion which is transparent to the electromagnetic radiation which encapsulates the capsule and contacts the first portion so no fluid can escape from the second portion except through the outlet tube.

9. A probe as described in claim 8 wherein the capsule defines a cylinder attached to the first portion from which the knobs extend and that defines a chamber which fluid from the inlet tube flows through.

10. A probe as described in claim 9 wherein the second portion includes one or more focusing elements which reshape the electromagnetic radiation.

11. A probe as described in claim 10 wherein the focusing element is chosen from the group consisting of a lens, mirror, lens/mirror combination, prism, and liquid crystal.

12. A probe as described in claim 11 including a fluid source connected to the inlet tube.

13. A probe as described in claim 12 wherein the fluid source includes a pump which pumps the fluid from the fluid source.

14. A probe as described in claim 13 wherein the fluid in the fluid source is selected from the group consisting of nitrogen, helium, C02, saline, water, D5W, lactated fingers or artificial blood.

15. A probe as described in claim 14 wherein the second portion includes a wart extending from the rotor.

16. A probe as described in claim 15 wherein the first portion includes a second radiation energy guide aligned to direct electromagnetic radiation to the wart that reflects the electromagnetic radiation back to the second radiation energy guide only when the tip of the second energy guide is aligned with the wart.

17. A probe as described in claim 1 wherein the second portion includes a mill having the rotor and the capsule.

18. A probe as described in claim 17 wherein the rotor includes a wheel.

19. A probe as described in claim 18 wherein the capsule holds the wheel.

20. A probe as described in claim 19 wherein the conduit is a radiation wave guide.

21. A probe as described in claim 20 wherein the radiation wave guide is an optical fiber.

22. A probe as described in claim 21 wherein the wheel includes a plug, and fins which extend radially from the plug, the fins pushed by the fluid causing the plug to rotate.

23. A probe as described in claim 22 wherein the capsule includes an inlet port and an outlet port.

24. A probe as described in claim 23 wherein the second portion has a reflecting material attached to the plug which redirects the electromagnetic radiation from the optical fiber.

25. A probe as described in claim 24 wherein the reflecting material includes a prism which reflects light from the optical fiber, the prism rotating with the plug.

26. A probe as described in claim 25 wherein the capsule includes a first pocket and a second pocket, in which a first end of the plug and a second end of the plug are respectfully disposed, the first and second pockets maintaining the plug in position in the capsule as the plug rotates.

27. A probe as described in claim 26 wherein the second portion includes a cover having at least a portion of which is transparent to the electromagnetic radiation which encapsulates the capsule and contacts the first portion so no fluid can escape from the second portion except through the outlet tube.

28. A probe as described in claim 27 including a fluid source connected to the inlet tube.

29. A probe as described in claim 28 wherein the fluid in the fluid source is selected from the group consisting of nitrogen, helium, saline, C02, D5W, lactated ringers, water or artificial blood.

30. A probe as described in claim 1, wherein the second portion is a nanomotor that includes a nanorotor, a nanostator, and a media structure formed with medium materials, the first portion includes a driving energy line via which driving energy is transmitted to the media structure, whereby the medium structure actuate the second portion by converting the driving energy into a reactive force between the nanostator and the nanorotor, wherein the second portion has a reflecting material attached to the nanorotor, thereby redirecting the electromagnetic radiation from the conduit, wherein the conduit is a radiation wave guide.

31. A probe as described in claim 30 wherein the medium materials are induced by the driving energy with osmotic pressure that provide the reactive force.

32. A probe as described in claim 31 wherein the medium materials include electrolyte and the driving energy is electricity energy.

33. A probe as described in claim 30 wherein the medium materials are induced by the driving energy with difference of surface tension that provide the reactive force.

34. A probe as described in claim 33 wherein the medium materials include water and the driving energy is radiation wave energy that generating heat.

35. A probe as described in claim 33 wherein the medium materials include water and the driving energy is electricity energy that generating heat.

36. A probe as described in claim 30 wherein the medium materials are induced by the driving energy with magnetic field variation that provide the reactive force.

37. A probe as described in claim 36 wherein the medium materials include conductive coils and the driving energy is electricity energy.

38. A method for imaging a patient comprising the steps of: inserting a catheter into the patient; and rotating a second portion of the catheter relative to a conduit extending through a first portion of the catheter, which redirects the electromagnetic radiation transmitted through the conduit to the patient and receives the electromagnetic radiation reflected back to the second portion from the patient and redirects the reflected electromagnetic radiation to the conduit; wherein the rotating step includes the step of flowing fluid through an inlet tube to the second portion to turn the second portion; wherein the rotating step includes the step of flowing fluid through the inlet tube to turn a rotor of the second portion, and wherein the rotating step includes the step of flowing the fluid against spiral shaped inner grooves which extend from a rotating center shaft of a turbine to create a rotating torque on the center shaft that causes the center shaft to rotate about the conduit that extends through the center shaft.

39. A method as described in claim 38 wherein the second portion has a reflecting material attached to the center shaft which redirects the electromagnetic radiation from the conduit.

40. A method as described in claim 39 wherein the conduit is a radiation waveguide.

41. A method as described in claim 40 wherein the radiation waveguide is an optical fiber.

42. A method as described in claim 41 wherein the reflecting material includes a prism which reflects light from the conduit, and including the step of rotating the prism with the center shaft as the center shaft is rotated by the flowing fluid.

43. A method as described in claim 42 wherein the rotating step includes the step of rotating the center shaft that is supported by knobs of a cylinder of the turbine in which the center shaft is disposed.

44. A method as described in claim 43 wherein the flowing step includes the step of flowing the fluid from the inlet tube through the chamber of the cylinder.

45. A method as described in claim 44 wherein the flowing step includes the step of removing the fluid flowing from the cylinder of the second portion through at least one outlet tube that extends through the first portion.

46. A method as described in claim 45 wherein the rotating direction and speed of the second portion are controlled by the pressure difference between the inlet and outlet.

47. A method as described in claim 45 wherein the first portion includes a second radiation energy guide aligned to direct electromagnetic radiation to the wart that reflects the electromagnetic radiation back to the second radiation energy guide only when the tip of the energy guide is aligned with the wart.

48. A method as described in claim 47 wherein the angular position of the second portion is monitored by the electromagnetic radiation guided by the second radiation energy guide.

49. A method for imaging a patient comprising the steps of: inserting a catheter into the patient and rotating a second portion of the catheter relative to a conduit extending through a first portion and the second portion of the catheter, which redirects the electromagnetic radiation transmitted through the conduit to the patient and receives the electromagnetic radiation reflected back to the second portion from the patient and redirects the reflected electromagnetic radiation to the conduit; wherein the rotating step includes the step of flowing fluid through an inlet tube to the second portion to turn the second portion; wherein the rotating step includes the step of flowing fluid through the inlet tube to turn a rotor of the second portion, and wherein the flowing step includes the step of flowing fluid through the inlet tube to turn a wheel of the rotor of a mill of the second portion.

50. A method as described in claim 49 wherein the flowing step includes the step of flowing the fluid against fins which extend from a rotating plug of the wheel to cause the wheel to rotate about the conduit that extends through the plug.

51. A method as described in claim 50 wherein the second portion has a reflecting material attached to the plug which redirects the electromagnetic radiation from the conduit.

52. A method as described in claim 51 wherein the conduit is an optical fiber.

53. A method as described in claim 52 wherein the reflecting material includes a prism which reflects light from the conduit, and including the step of rotating the prism with the plug as the wheel is rotated by the flowing fluid.

54. A method as described in claim 53 wherein the rotating step includes the step of rotating the wheel that is disposed in pockets of a capsule of the mill in which the wheel is disposed.

55. A method as described in claim 54 wherein the flowing step includes the step of flowing the fluid from the inlet tube through an inlet port of the capsule into the capsule.

56. A method as described in claim 55 wherein the flowing step includes the step of removing the fluid flowing from an outlet port of the capsule of the second portion through at least one outlet tube that extends through the first portion so a rotational flow path is created with the fluid through the capsule which rotates the wheel as the fluid flows against the fins.

57. A method as described in claim 56 wherein the rotating direction and speed of the second portion are controlled by pressure difference between the inlet and outlet.

58. A method as described in claim 56 wherein the first portion includes a second radiation energy guide aligned to direct energy to a wart that reflects the electromagnetic radiation back to the second radiation energy guide only when the tip of the second energy guide is aligned with the wart.

59. A method as described in claim 58 wherein the angular position of the second portion is monitored by the radiation energy guided by the second radiation energy guide.

* * * * *